United States Patent
Dumitrescu et al.

(10) Patent No.: US 6,716,787 B1
(45) Date of Patent: Apr. 6, 2004

(54) POLYMERISATION CATALYST

(75) Inventors: Anca Dumitrescu, Toulouse (FR); Heinz Gornitzka, Pompertuzat (FR); Blanca Martin-Vaca, Toulouse (FR); Didier Bourissou, Plaisance du Touch (FR); Guy Bertrand, Riverside, CA (US); Jean-Bernard Cazaux, Aramon (FR)

(73) Assignees: Societe de Conseils de Recherches et d'Applications Scientifiques (S.C.R.A.S.) (FR); Centre National de la Recherche Scientifique (C.N.R.S.) (FR)

( * ) Notice: Subject to any disclaimer, the term of this patent is extended or adjusted under 35 U.S.C. 154(b) by 57 days.

(21) Appl. No.: 10/018,646

(22) PCT Filed: Jun. 23, 2000

(86) PCT No.: PCT/FR00/01752
§ 371 (c)(1),
(2), (4) Date: Dec. 18, 2001

(87) PCT Pub. No.: WO01/00630
PCT Pub. Date: Jan. 4, 2001

(30) Foreign Application Priority Data

Jun. 25, 1999 (EP) ............................................ 99401584

(51) Int. Cl.$^7$ ............................ C07F 7/10; C07F 9/535; C08G 59/70; C08G 63/84; C08G 63/87
(52) U.S. Cl. ......................... 502/155; 534/15; 556/12; 556/18; 556/20; 556/21; 556/22; 556/23; 556/404; 556/410; 502/152; 502/153
(58) Field of Search ................................. 502/155, 152, 502/153; 556/12, 18, 20, 21, 22, 23, 404, 410; 534/15

(56) References Cited

U.S. PATENT DOCUMENTS

| | | | | |
|---|---|---|---|---|
| 5,202,493 A | * | 4/1993 | Burk | 568/12 |
| 5,344,948 A | * | 9/1994 | Verkade | 556/51 |
| 6,281,154 B1 | * | 8/2001 | Bertrand et al. | 502/150 |
| 6,303,807 B1 | * | 10/2001 | Bertrand et al. | 556/81 |

OTHER PUBLICATIONS

Chemical abstracts accession No. 134:72043 for priority application Nos. EP 1999–401584 (Jun. 25, 1999) and PCT WO 2000–FR175 (Jun. 23, 2000) corresponding to the instant application, registry No. 314256–72–9.*

Hubert–Pfalzgraf, L.G. et al. "Synthesis and characterization of volatile cerium (IV) hexaflourisopropoxide complexes. Structure of (hpmdien)2Ce(och(cf3)2)6" Journal of the Chemical Society, Dalton Transaction, 1982 pp. 1929–1932.

Britovsek, G .P. et al., "The search for new–generation olefin polymerization catalysts: life beyond metallocenes" Angewandte Chemie International Edition, English 1999, pp. 428–447.

* cited by examiner

*Primary Examiner*—Robert Sellers
(74) *Attorney, Agent, or Firm*—Muserlian, Lucas and Mercanti

(57) ABSTRACT

A subject of the present invention is new compounds having a lanthanide and having a tridentate ligand, a process for their preparation and their use in particular as polymerization catalysts.

8 Claims, 1 Drawing Sheet

POLYMERISATION CATALYST

Figure 1:
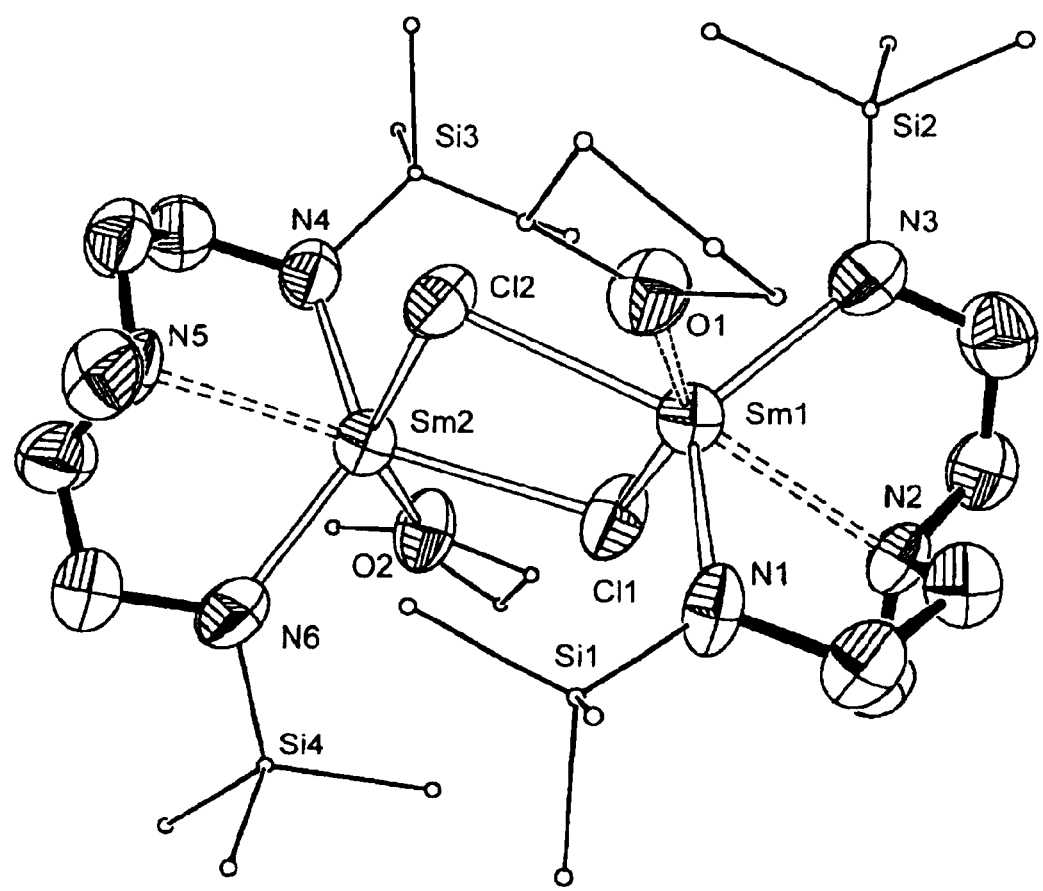

This application is a 371 of PCT FR00/01752 filed Jun. 23, 2000.

The present invention relates to new compounds having a lanthanide and a tridentate ligand, a process for their preparation and their use in particular as polymerization catalysts.

The use of the lanthanide derivatives as catalysts for polymerization and copolymerization of olefines (Gibson et al., Angew. Chem., Int. Ed. Engl., (1999) 38, 428) and heterocycles (Yao et al., J. Polymer. Sci. Part A: Polymer Chem., (1996) 34, 1799) is known.

However, it has been shown that each type of catalyst used for polymerizations or copolymerizations produces respectively different polymers or copolymers in particular because of transesterification reactions which lead to inversions of the stereogenic centres (Jedlinski et al., Macromolecules, (1990) 191, 2287; Munson et al., Macromolecules, (1996) 29, 8844; Montaudo et al., Macromolecules, (1996) 29, 6461). The problem is therefore to find new catalytic systems in order to obtain new polymers or copolymers, and more particularly block copolymers. The use of catalytic systems making it possible to obtain block copolymers, allows control of the chain formation of the monomers in order to obtain specific copolymers having the appropriate properties. This is particularly useful for biocompatible copolymers, the biodegradation of which is influenced by this chain formation.

Therefore a subject of the invention is the products of general formula 1

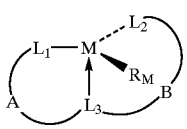

(1)

in which

M represents a lanthanide;

$R_M$ represents the hydrogen atom, a halogen atom or an alkyl, cycloalkyl, aryl, alkoxy, cycloalkoxy, aryloxy, alkylthio, cycloalkylthio, arylthio, amino, alkylamino, dialkylamino, cycloalkylamino, di(cycloalkyl)amino, alkyl(cycloalkyl)amino, arylamino, diarylamino, alkylarylamino or (cycloalkyl)arylamino radical;

A and B represent, independently, a carbon chain with 2 to 4 carbon atoms, optionally substituted by one of the following substituted (by one or more identical or different substituents) or non-substituted alkyl, cycloalkyl or aryl radicals, in which said substituent is a halogen atom, the alkyl, nitro or cyano radical;

$L_1$, $L_2$ and $L_3$ represent, independently, a group of formula —$E_{15}(R_{15})$— in which $E_{15}$ is an element of group 15 and $R_{15}$ represents the hydrogen atom; one of the following substituted (by one or more identical or different substituents) or non-substituted alkyl, cycloalkyl or aryl radicals, in which said substituent is a halogen atom, the alkyl, nitro or cyano radical; a radical of formula —$E_{14}RR'R''$ in which $E_{14}$ is an element of group 14 and R, R' and R'' represent, independently, the hydrogen atom or one of the following substituted (by one or more identical or different substituents) or non-substituted alkyl, cycloalkyl, aryl, alkoxy, cycloalkoxy, aryloxy, alkylthio, cycloalkylthio or arylthio radicals in which said substituent is a halogen atom, the alkyl, nitro or cyano radical; or a radical of formula —$SO_2R'_{15}$ in which $R'_{15}$ represents a halogen atom, an alkyl, haloalkyl or aryl radical optionally substituted by one or more substituents chosen from the alkyl, haloalkyl and halogen radicals.

In the definitions indicated above, the expression halogen represents a fluorine, chlorine, bromine or iodine atom, preferably chlorine. The expression alkyl preferably represents a linear or branched alkyl radical having 1 to 6 carbon atoms and in particular an alkyl radical having 1 to 4 carbon atoms such as the methyl, ethyl, propyl, isopropyl, butyl, isobutyl, sec-butyl and tert-butyl radicals.

The term haloalkyl preferably designates radicals in which the alkyl radical is as defined above and is substituted by one or more halogen atoms as defined above such as, for example, bromoethyl, trifluoromethyl, trifluoroethyl or also pentafluoroethyl. The alkoxy radicals can correspond to radicals in which the alkyl radical is as defined above. The methoxy, ethoxy, isopropyloxy or tert-butyloxy radicals are preferred. The alkylthio radicals preferably represent radicals in which the alkyl radical is as defined above such as, for example, methylthio or ethylthio. The alkylamino and dialkylamino radicals preferably represent radicals in which the alkyl radical is as defined above such as, for example, methylamino or dimethylamino.

The cycloalkyl radicals are chosen from the saturated or unsaturated monocyclic cycloalkyls. The saturated monocyclic cycloalkyl radicals can be chosen from radicals having 3 to 7 carbon atoms such as the cyclopropyl, cyclobutyl, cyclopentyl, cyclohexyl or cycloheptyl radicals. The unsaturated cycloalkyl radicals can be chosen from the cyclobutene, cyclopentene, cyclohexene, cyclopentadiene or cyclohexadiene radicals. The cycloalkoxy radicals can correspond to radicals in which the cycloalkyl radical is as defined above. The cyclopropyloxy, cyclopentyloxy or cyclohexyloxy radicals are preferred. The cycloalkylthio radicals can correspond to radicals in which the cycloalkyl radical is as defined above, such as for example cyclohexylthio. The cycloalkylamino and di(cycloalkyl)amino radicals can correspond to radicals in which the cycloalkyl radical is as defined above such as for example cyclohexylamino and di(cyclohexyl)amino.

The aryl radicals can be of mono or polycyclic type. The monocyclic aryl radicals can be chosen from the phenyl radicals optionally substituted by one or more alkyl radicals, such as tolyl, xylyl, mesityl, cumenyl. The polycyclic aryl radicals can be chosen from the naphthyl, anthryl, phenanthryl radicals. The aryloxy radicals can correspond to radicals in which the aryl radical is as defined above. The phenoxy, 2,4,6-tritertiobutylphenoxy, tolyloxy or mesityloxy radicals are preferred. The arylthio radicals preferably designate radicals in which the aryl radical is as defined above such as for example in phenylthio. The arylamino and diarylamino radicals preferably designate radicals in which the aryl radical is as defined above such as, for example, phenylamino or diphenylamino.

The alkyl(cycloalkyl)amino radicals can correspond to radicals in which the alkyl and cycloalkyl radicals are as defined above such as, for example methyl(cyclohexyl) amino. The alkylarylamino radicals preferably designate radicals in which the alkyl and aryl radicals are as defined above such as, for example methylphenylamino. The (cycloalkyl)arylamino radicals can correspond to radicals in which the cycloalkyl and aryl radicals are as defined above such as, for example (cyclohexyl)phenylamino.

The compounds of formula 1 can be presented in the form of a monomer or of a dimer and more particularly the compounds of formula 1 in which M represents a samarium atom are generally presented in the form of a dimer.

A more particular subject of the invention is the products of general formula 1 as defined above, characterized in that $R_M$ represents a halogen atom; A and B represent, independently, a carbon chain with 2 to 4 carbon atoms; $L_1$, $L_2$ and $L_3$ represent, independently, a radical of formula —$E_{15}(R_{15})$— in which $E_{15}$ is a nitrogen or phosphorus atom and $R_{15}$ represents an alkyl radical or a radical of formula —$E_{14}RR'R''$ in which $E_{14}$ represents a carbon or silicon atom and R, R' and R" represent, independently, the hydrogen atom or an alkyl radical.

Preferably, M represents a samarium atom. Preferably also, $R_M$ represents a chlorine atom; A and B represent, independently, a carbon chain with 2 carbon atoms; $L_1$, $L_2$ and $L_3$ represent, independently, a radical of formula —$E_{15}$ ($R_{15}$)— in which $E_{15}$ is a nitrogen atom and $R_{15}$ represents a methyl, ethyl, propyl, isopropyl radical or a radical of formula —$E_{14}RR'R''$ in which $E_{14}$ represents a silicon atom and R, R' and R" represent, independently, the hydrogen atom or a methyl, ethyl, propyl or isopropyl radical.

A more particular subject of the invention is the product described hereafter in the examples, in particular the product corresponding to the following formula:

—[(Me$_3$SiNCH$_2$CH$_2$)$_2$NMe]SmCl.

A subject of the invention is also a process for the preparation of the products of general formula 1 as defined above, characterized in that a product of formula I

$(L_1-A-L_3-B-L_2)^{2-}, 2Y^+$ (I)

in which $L_1$, A, $L_3$, B and $L_2$ have the meanings indicated above and Y represents the hydrogen atom, a metal or an organometallic group, is reacted with a product of formula II

$MR_MZ_1Z_2$ (II)

in which M and $R_M$ have the meanings indicated above and $Z_1$ and $Z_2$ represent, independently, a parting group, in order to obtain a product of formula I as defined above.

The reaction of a compound of general formula I with a compound of general formula II in order to obtain a compound of general formula 1, can be carried out under an inert atmosphere such as under a freon or argon atmosphere, in an aprotic solvent, at a temperature comprised between −90 and +50° C. The compounds I thus obtained are purified by standard purification methods.

As aprotic solvent, the aromatic hydrocarbons such as benzene, toluene; the aliphatic hydrocarbons such as pentane, heptane, hexane, cyclohexane; ethers such as diethylether, dioxane, tetrahydrofuran or ethyltertiobutyl ether can be used.

The compounds of formula 1 can comprise one or more coordinating solvent molecules used during the preparation process. The expression coordinating solvent represents an aromatic hydrocarbon such as benzene, toluene; a cyclic or acyclic dialkyl ether such as diethylether, dioxane, tetrahydrofuran, ethylterbutylether; a chlorinated solvent such as dichloromethane, chloroform; an aliphatic or aromatic nitrile such as acetonitrile, benzonitrile; an aliphatic or aromatic, cyclic or acyclic ketone such as acetone, acetophenone, cyclohexanone; an aliphatic or aromatic, cyclic or acyclic carboxylic acid derivative, such as ethyl acetate or dimethylformamide.

In compounds I, Y represents the hydrogen atom, a metal or a metallic group. The metallic group can be a compound of formula $R'''M_1$ or $R'''_3M_2$ in which $R'''$ represents a halogen atom or indifferently an alkyl, cycloalkyl, aryl, alkoxy, cycloalkoxy or aryloxy radical as previously defined, $M_1$ is an alkaline-earth such as magnesium or a zinc or mercury atom and $M_2$ a tin or lead atom; preferably, the metallic group is chosen from the MgBr, ZnMe, SnMe$_3$, SnBu$_3$ or PbMe$_3$ groups. The metal can be an alkali metal chosen from lithium, sodium or potassium.

In compounds II, $Z_1$ and $Z_2$ represent, independently, a parting group such as a halogen atom, an alkyl, cycloalkyl, alkoxy, aryl or aryloxy group as previously defined, or also a methanesulphonyloxy, a benzenesulphonyloxy, p-toluenesulphonyloxy.

The starting products of formula I are known products or can be prepared from known products. For their synthesis, the following references can be mentioned: Cloke et al., J. Chem. Soc., Dalton Trans. (1995) 25; Wilkinson and Stone, Comprehensive Organometallic Chemistry (1982) vol. 1, 557.

The products of formula II are commercially available or can be manufactured by methods known to a person skilled in the art.

A subject of the invention is also the use of the products of formula 1 as defined above, as catalysts for carrying out (co)polymerization, that is to say polymerization or copolymerization. Whilst carrying out (co)polymerization, the compounds according to the invention also play the role of chain initiator and/or regulator.

The compounds of formula 1 are particularly useful for carrying out the polymerization of heterocycles. The heterocycles can contain one or more heteroatoms of groups 15 and/or 16, and are from three to eight members in size. As an example of heterocycles corresponding to the aforementioned formulation, epoxides, thioepoxides, cyclic esters or thioesters such as the lactones, the lactames and the anhydrides can be mentioned.

The compounds of formula 1 are also particularly useful for carrying out the (co)polymerization of cyclic esters. As an example of cyclic esters, the polymer cyclic esters of lactic and/or glycolic acid can be mentioned. Random or block copolymers can be obtained depending on whether monomers are introduced together at the start of the reaction, or sequentially during the reaction.

A subject of the invention is also a process for the preparation of random or block copolymers or polymers, which consists of bringing a polymerization catalyst and optionally a polymerization solvent into contact with one or more monomers, a chain initiator and/or regulator, the said process characterized in that the chain initiator and/or the regulator and the polymerization catalyst are represented by the same compound which is chosen from the compounds of formula (1) as defined above.

The (co)polymerization can be carried out either in solution or in supercooling. When the (co)polymerization is carried out in solution, the reaction solvent can be the (or one of the) substrate(s) used in the catalytic reaction. Solvents which do not interfere with the catalytic reaction itself are also suitable. As an example of such solvents, saturated or aromatic hydrocarbons, ethers, aliphatic or aromatic halides can be mentioned.

The reactions are carried out at temperatures comprised between ambient temperature and approximately 250° C.; the temperature range comprised between 40 and 200° C. proves most advantageous. The durations of the reactions are comprised between a few minutes and 300 hours, and preferably between 5 minutes and 72 hours.

This (co)polymerization process is particularly suitable for obtaining a (co)polymer of cyclic esters, in particular the polymer cyclic esters of lactic and/or glycolic acid. The products obtained such as biodegradable lactic, glycolic, copolymer are advantageously used as a support in sustained release therapeutic compositions. The process is also particularly suitable for the polymerization of epoxides, in particular propene oxide. The polymers obtained are compounds which can be used for the synthesis of organic liquid crystals or also as semi-permeable membranes.

The invention also relates to polymers or copolymers which can obtained by carrying out a process such as described above. The polydispersity (Mw/Mn) of the (co) polymers thus obtained can be modified by leaving the reaction mixture at the reaction temperature after total conversion of the monomer(s). The masses of the (co) polymers are little affected during this process. These phenomenon are due to the inter- or intra-molecular transesterification reactions (Kiecheldorf et al., Macromolecules, (1988) 21, 286).

The following examples are given to illustrate the above procedures and should in no way be considered as limiting the scope of the invention.

EXAMPLE 1

[(Me$_3$SiNCH$_2$CH$_2$)$_2$NMe]SmCl (in the Form of a Dimer with a Molecule of tetrahydrofuran Coordinated on Each Metallic Centre)

M=Sm; R$_M$=Cl; A=B=—CH$_2$CH$_2$—; L$_1$=L$_2$=NSiMe$_3$; L$_3$=NMe 1.22 g (4.7 mmol) of [(Me$_3$SiNCH$_2$CH$_2$)$_2$NMe]$^{2-}$, 2Li$^+$ and 10 ml of tetrahydrofuran are introduced successively into a Schlenk tube equipped with magnetic stirrer and purged under argon. The reaction mixture is cooled down to –78° C., then a suspension of 1.20 g (4.7 mmol) of SmCl$_3$ in tetrahydrofuran is introduced. The reaction mixture is returned to ambient temperature then left under agitation for 4 hours at ambient temperature. After the solvent is evaporated off, the residue is taken up with toluene then filtered. After the solvent is evaporated off, a white solid is obtained. The desired compound is isolated in the form of white crystals by crystallization at –20° C. from toluene (5 ml) (yield 70%). This compound is characterized by multinuclear magnetic resonance spectroscopy and X-ray diffraction (FIG. 1 and Table 1 below). Melting point: 173° C.

EXAMPLE 2

Preparation of an Random (D,L-lactide/glycolide) Copolymer with a lactide/glycolide Composition Close to 70/30

0.05 g (0.1 mmol) of [(Me$_3$SiNCH$_2$CH$_2$)$_2$NMe]SmCl, 2.1 g (14.6 mmol) of D,L-lactide and 0.72 g (6.2 mmol) of glycolide are introduced successively into a Schlenk tube equipped with magnetic stirrer and purged under argon. The reaction mixture is left under agitation at 180° C. for 1 hour. Analysis by proton NMR allows verification that the conversion of the monomer is 93% lactide and 94% glycolide. The ratio of the signal integrals corresponding to the polylactide part (5.20 ppm) and the polyglycolide part (4.85 ppm) makes it possible to evaluate the composition of the copolymer at 66% lactide and 34% glycolide. According to a GPC analysis, using a calibration carried out from polystyrene standards of masses 761 to 400000, this copolymer is a mixture of macromolecules (Mw/Mn=2.95) of fairly high masses (Mw=37500 Dalton).

EXAMPLE 3

Preparation of an Random (D,L-lactide/glycolide) Copolymer with a lactide/glycolide Composition Close to 50/50

40 mg (0.08 mmol) of [(Me$_3$SiNCH$_2$CH$_2$)$_2$NMe]SmCl, 1.87 g (13 mmol) of D,L-lactide and 1.48 g (13 mmol) of glycolide and 4 ml of mesitylene are introduced successively into a Schlenk tube equipped with a magnetic stirrer and purged under argon. The reaction mixture is left under agitation at 180° C. for 4 hours. Analysis by proton NMR allows verification that the conversion of the monomers is 100% lactide and 100% glycolide. The ratio of the signal integrals corresponding to the polylactide part (5.20 ppm) and the polyglycolide part (4.85 ppm) makes it possible to evaluate the composition of the copolymer at 50% lactide and 50% glycolide. According to a GPC analysis, using a scale created from PS standards of masses 761 to 400 000, this copolymer is a mixture of macromolecules (Mw/Mn= 1.53) of high masses (Mw=34000 Dalton).

EXAMPLE 4

Preparation of an Random (D,L-lactide/glycolide) Copolymer of High Masses 0.05 g (0.1 mmol) of [(Me$_3$SiNCH$_2$CH$_2$)$_2$NMe]SmCl, 2.1 g (14.6 mmol) of D,L-lactide and 0.72 g (6.2 mmol) of glycolide are introduced successively into a Schlenk tube equipped with magnetic stirrer and purged under argon. The reaction mixture is left under agitation at 160° C. for 30 minutes. Analysis by proton NMR allows verification that the conversion of the monomers is 71% lactide and 100% glycolide. The ratio of the signal integrals corresponding to the polylactide part (5.20 ppm) and the polyglycolide part (4.85 ppm) allows the composition of the copolymer to be evaluated at 61% lactide and 39% glycolide. According to a GPC analysis, using a calibration carried out from PS standards of masses 761 to 400000, this copolymer is a mixture of macromolecules (Mw/Mn=1.56) of high masses (Mw=169000 Dalton).

EXAMPLE 5

Modification of the Composition, of Mass and of the Polydispersity of a (D,L-lactide/glycolide) Copolymer 0.050 g (0.1 mmol) of [(Me$_3$SiNCH$_2$CH$_2$)$_2$NMe]SmCl 2.095 g (10.1 mmol) of D,L-lactide and 1.68 g (10.1 mmol) of glycolide are introduced successively into a Schlenk tube equipped with magnetic stirrer and purged under argon. The reaction mixture is left under agitation at 160° C. After 1 hour, the conversion of the monomers is 44% lactide and an 100% glycolide according to an analysis by proton NMR and the ratio of the signal integrals corresponding to the polylactide part (5.20 ppm) and the polyglycolide part (4.85 ppm) makes it possible to evaluate the composition of the copolymer at 42% lactide and 58% glycolide. According to a GPC analysis, using a calibration carried out from PS standards of masses 761 to 400000, this copolymer is a mixture of macromolecules (Mw/Mn=1.73) of fairly high masses (Mw=28265 Dalton). After an additional 2 hours 30 minutes at 160° C., the lactide conversion reaches 96%. The composition of the copolymer is then 49% lactide and 51% glycolide. The GPC analysis of an aliquot shows that the dispersity and the mass have increased (Mw/Mn=1.84; Mw=47200 Dalton).

TABLE 1

Length of selected bonds (in Angstrom) and bond
angles (in degrees) for the compound of Example 1

| Sm(1)—N(1) | 2.290 (12) Å | N(2)—C(6) | 1.516 (17) Å |
|---|---|---|---|
| Sm(1)—N(2) | 2.574 (9) Å | N(2)—C(7) | 1.482 (17) Å |
| Sm(1)—N(3) | 2.299 (12) Å | C(7)—C(8) | 1.50 (2) Å |
| N(1)—Si(1) | 1.678 (12) Å | C(8)—N(3) | 1.461 (18) Å |
| N(3)—Si(2) | 1.695 (12) Å | Sm(1)—O(1) | 2.519 (8) Å |
| N(1)—C(4) | 1.494 (17) Å | Sm(1)—Cl(1) | 2.773 (3) Å |
| C(4)—C(5) | 1.508 (19) Å | Sm(1)—Cl(2) | 2.797 (3) Å |
| C(5)—N(2) | 1.470 (16) Å | | |
| N(1)—Sm(1)—N(2) | 68.9 (3)° | Sm(1)—N(1)—C(4) | 116.5 (8)° |
| N(2)—Sm(1)—N(3) | 71.5 (4)° | Sm(1)—N(3)—C(8) | 118.7 (9)° |
| N(1)—Sm(1)—N(3) | 124.1 (4)° | Sm(1)—N(2)—C(5) | 97.7 (7)° |
| N(1)—Sm(1)—Cl(1) | 104.0 (3)° | Sm(1)—N(2)—C(6) | 121.1 (8)° |
| N(1)—Sm(1)—Cl(2) | 122.1 (3)° | Sm(1)—N(2)—C(7) | 107.0 (7)° |

What is claimed is:

1. A compound of the formula

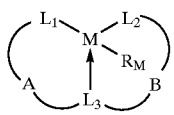 (1)

wherein

M is lanthanide;

$R_M$ is selected from the group consisting of hydrogen, halogen, alkyl, cycloalkyl, aryl, alkoxy, cycloalkoxy, aryloxy, alkylthio, cycloalkylthio, arylthio, amino, alkylamino, dialkylamino, cycloalkylamino, di(cycloalkyl)amino, alkyl(cycloalkyl)amino, arylamino, diarylamino, alkylarylamino and (cycloalkyl)arylamino;

A and B are, independently, a carbon chain of 2 to 4 carbon atoms, optionally substituted by at least one member of the group consisting of substituted or non-substituted alkyl, cycloalkyl and aryl, the substituents being selected from the group consisting of halogen, alkyl, nitro and cyano; $L_1$, $L_2$ and $L_3$ are independently $E_{15}(R_{15})$—, in which $E_{15}$ is an element of group 15 of the Periodic Table and $R_{15}$ is selected from the group consisting of i) hydrogen, ii) substituted or non-substituted alkyl, cycloalkyl and aryl, in which said substituent is selected from the group consisting of halogen, alkyl, nitro, and cyano; iii) $E_{14}RR^1R^{11}$ wherein $E_{14}$ is an element of group 14 of the Periodic Table and R, $R^1$ and $R^{11}$ are independently; selected from the group consisting of hydrogen, substituted or non-substituted alkyl, cycloalkyl, aryl, alkoxy, cycloalkoxy, aryloxy, alkylthio, cycloaikylthio and arylthio, in which said substituent is at least one member of the group consisting of halogen, alkyl, nitro and cyano; iv) —$SO_2R'_{15}$ in which $R^1{}_{15}$ is selected from the group consisting of halogen, alkyl, haloalkyl and aryl optionally substituted by at least one member of the group consisting of alkyl, haloalkyl and halogen.

2. A compound of claim 1, in the form of a monomer or a dimer.

3. A compound of claim 1 wherein $R_M$ is halogen; A and B are independently, a carbon with 2 to 4 carbon atoms, $L_1$, $L_2$ and $L_3$ are independently, —$E_{15}(R_{15})$— in which $E_{15}$ is nitrogen or phosphorus and $R_{15}$ is alkyl or —$E_{14}RR^1RR^{11}$. $E_{14}$— is carbon or silicon and R, $R^1$ and $R^{11}$ are independently, hydrogen or alkyl.

4. A compound of claim 1 wherein M is samarium.

5. A compound of claim 1 wherein $R_M$ is chlorine; A and B are independently, a carbon chain with 2 carbon atoms; $L_1$, $L_2$ and $L_3$ are independently, —$E_{15}(R_{15})$— in which $E_{15}$ is nitrogen and $R_{15}$ is selected from the group consisting of methyl, ethyl, propyl, isopropyl and $E_{14}RR^1R^{11}$, $E_{14}$ is silicon and R, $R^1$ and $R^{11}$ are independently selected from the group consisting of hydrogen, methyl, ethyl, propyl and isopropyl.

6. A compound of claim 1 being

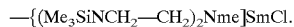

7. A compound of claim 6, in the form of a dimer.

8. A process for the preparation of a compound of claim 1, comprising reacting a compound of the formula

 (I)

in which $L_1$, A, $L_3$, B and $L_2$ are as defined in claim 1 and Y is hydrogen or a metal or an organometalic with a product of the formula

 (II)

in which M and $R_M$ are as defined in claim 1 and $Z_1$ and $Z_2$ are independently, parting groups to obtain a product of claim 1.

* * * * *